United States Patent [19]
Haddad et al.

[11] Patent Number: 5,229,128
[45] Date of Patent: Jul. 20, 1993

[54] DRUG DELIVERY OPHTHALMIC INSERT AND METHOD OF PREPARING SAME

[76] Inventors: Heskel M. Haddad, 1200 Fifth Ave., New York, N.Y. 10029; Spiro P. Loucas, 16 Toni Ct., Plainview, N.Y. 11803

[21] Appl. No.: 770,132

[22] Filed: Oct. 1, 1991

Related U.S. Application Data

[63] Continuation of Ser. No. 291,426, Dec. 23, 1988, abandoned, which is a continuation of Ser. No. 873,021, Jun. 11, 1986, abandoned.

[51] Int. Cl.$^5$ .................. B29B 9/06; B28B 3/20; A61F 2/14; A61K 9/14
[52] U.S. Cl. .................. 424/427; 424/428; 424/429; 264/1.1; 264/1.6; 264/2.6; 264/13; 264/176.1; 514/777; 514/779; 523/106
[58] Field of Search ............ 523/106; 424/423, 426, 424/425, 427, 429, 78.04, 428; 264/1.1, 1.6, 2.6, 13, 176.1; 514/777, 779

[56] References Cited

U.S. PATENT DOCUMENTS

| | | | |
|---|---|---|---|
| Re. 30,368 | 8/1980 | Loshaek et al. | 351/160 |
| 3,558,774 | 1/1971 | Michaels et al. | 264/2.6 X |
| 3,767,788 | 10/1973 | Rankin | 424/78 |
| 3,845,201 | 10/1974 | Haddad et al. | 604/894 |
| 3,856,919 | 12/1974 | Rankin | 424/78 |
| 3,863,633 | 2/1975 | Ryde et al. | 424/78 |
| 3,867,519 | 2/1975 | Michaels | 424/422 |
| 3,868,445 | 2/1975 | Ryde et al. | 424/78 |
| 3,960,150 | 6/1976 | Hussain et al. | 128/260 |
| 3,963,025 | 6/1976 | Whitaker et al. | 128/260 |
| 3,968,201 | 7/1976 | Ryde et al. | 424/78 |
| 3,993,071 | 11/1976 | Higuchi et al. | 128/260 |
| 4,120,949 | 10/1978 | Bapatha et al. | 424/78 |
| 4,179,497 | 12/1979 | Cohen et al. | 604/294 |
| 4,287,175 | 9/1981 | Katz | 424/78 |
| 4,343,787 | 8/1982 | Katz | 604/894 |
| 4,346,197 | 8/1982 | Crano et al. | 525/277 |
| 4,650,616 | 3/1987 | Wajs | 523/106 X |
| 4,686,222 | 8/1987 | Atkinson et al. | 514/255 |
| 4,771,089 | 9/1988 | Ofstead | 523/106 X |
| 4,921,884 | 5/1990 | Hammer et al. | 523/106 |

FOREIGN PATENT DOCUMENTS 1529143  10/1978  United Kingdom ............ 604/294

*Primary Examiner*—Thurman K. Page
*Assistant Examiner*—Carlos Azpuru
*Attorney, Agent, or Firm*—Rosenman & Colin

[57] ABSTRACT

A drug delivery ophthalmic insert prepared by forming a water soluble solid polymer into a paste by the addition of a small fixed amount of water, drying the paste and then sectioning the paste into a plurality of rod shaped inserts is provided. The insert is rendered suitable for prolonged and sustained delivery of medication to the eye since it is formed by the addition of a small amount of water and has a surface area less than about 3 mm$^2$. Specific water soluble solid polymers which may be used include methylcellulose, hydroxyethyl cellulose, alginic acid and combinations thereof as well as mixtures of pilocarpine dispersed in methylcellulose and its combinations.

17 Claims, 2 Drawing Sheets

DRUG DELIVERY OPHTHALMIC INSERT AND METHOD OF PREPARING SAME

This is a continuation of application Ser. No. 07/291,426, filed Dec. 23, 1988, now abandoned, which is a continuation of application Ser. No. 06/873,021, filed Jun. 11, 1986, now abandoned.

BACKGROUND OF THE INVENTION

This invention relates to a method for manufacturing solid drug delivery ophthalmic inserts. More particularly, the method involves the preparation of rod shaped inserts used for the treatment of dry eyes and ophthalmic diseases by forming a paste gel by the addition of controlled increments of water to a hydrophilic water soluble polymer.

Conventional ophthalmic drug delivery methods utilize liquid drops, ointment or suspension type installation in order to evoke the desired therapeutic response. Although effective in treating ocular diseases, these methods have specific disadvantages. A patient may lose a substantial portion of the medicine due to poor delivery technique or to involuntary tearing following installation. Additionally, many patients may not adhere to the physician's prescribed regimen for daily treatment. Furthermore, if drug delivery is required more than once or twice a day, the patient may be inconvenienced while away from home.

A more recent development relates to a water soluble solid ophthalmic insert for the treatment of dry eyes composed of a water soluble polymer of appropriate size which can be placed in the cul-de-sac of the eye. The insert is prepared by completely dissolving particles of the polymer in water and subsequently evaporating all the water in order to form a solid insert.

However, this method does not produce a sufficiently sustained therapeutic response for the treatment of various eye diseases. Since inserts of water soluble solid polymer are formed by completely dissolving the starting drug particles in excess water, significant amounts of water are retained by the dosage form even after drying. Additionally, if the shape of the inserts is circular and dimensionally thin, a large surface area remains in contact with the lacrimal fluid in the eye after application. These features contribute to rapid dissolution and release of the product when treating eye disease.

Accordingly, it is desirable to provide an improved method for ophthalmic drug delivery having a more prolonged and sustained delivery of the required medicinal dosage.

SUMMARY OF THE INVENTION

Generally speaking, in accordance with the invention, a method for manufacturing a drug delivery rod insert is provided. Specifically, the drug delivery rod insert is manufactured by forming a water soluble solid polymer into a paste by the addition of fixed increments of water. The paste is dried at room temperature. Thereafter, the dried paste is sectioned to form cylindrical rod shaped inserts which are packaged in an empty gelatin capsule. In a preferred embodiment, each dry rod insert has a surface area less than about 2.7 square millimeters based on a diameter of 0.65 mm and an arbitrary length of 1 mm.

Specific water soluble solid polymers which may be used in the invention include, but are not limited to, methylcellulose, hydroxyethyl cellulose, alginic acid, a mixture of pilocarpine dispersed in methylcellulose and combinations of these polymers.

The drug delivery rod insert described herein can be used for the treatment of various eye syndromes including keratoconjunctivitis sicca, exposure type keratitis and glaucoma. Additionally, the rod insert may be employed with drugs which relieve eye itching and burning sensations due to the presence of extraneous bodies in the corneal area.

Accordingly, it is an object of the invention to provide an improved method for manufacturing a drug delivery rod insert.

Another object of the invention is to provide an improved method for manufacturing a drug delivery rod insert used for the treatment of dry eyes.

A further object of the invention is to provide an improved drug delivery rod insert to be used for the treament of ocular disease.

Still another object of the invention is to provide an improved drug delivery rod insert which provides prolonged and sustained delivery of the drug that is incorporated into the insert.

Yet a further object of the invention is to provide an improved drug delivery rod insert having significantly less water than that contained in prior art rod inserts.

Another object of the invention is to provide an improved drug delivery rod insert having minimal surface area.

Still other objects and advantages of the invention will, in part, be obvious and will, in part, be apparent from the specification.

The invention accordingly comprises the several steps and the relation of one or more such steps with respect to each of the others, and the composition possessing the features, properties and the relation of components which are exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 1:
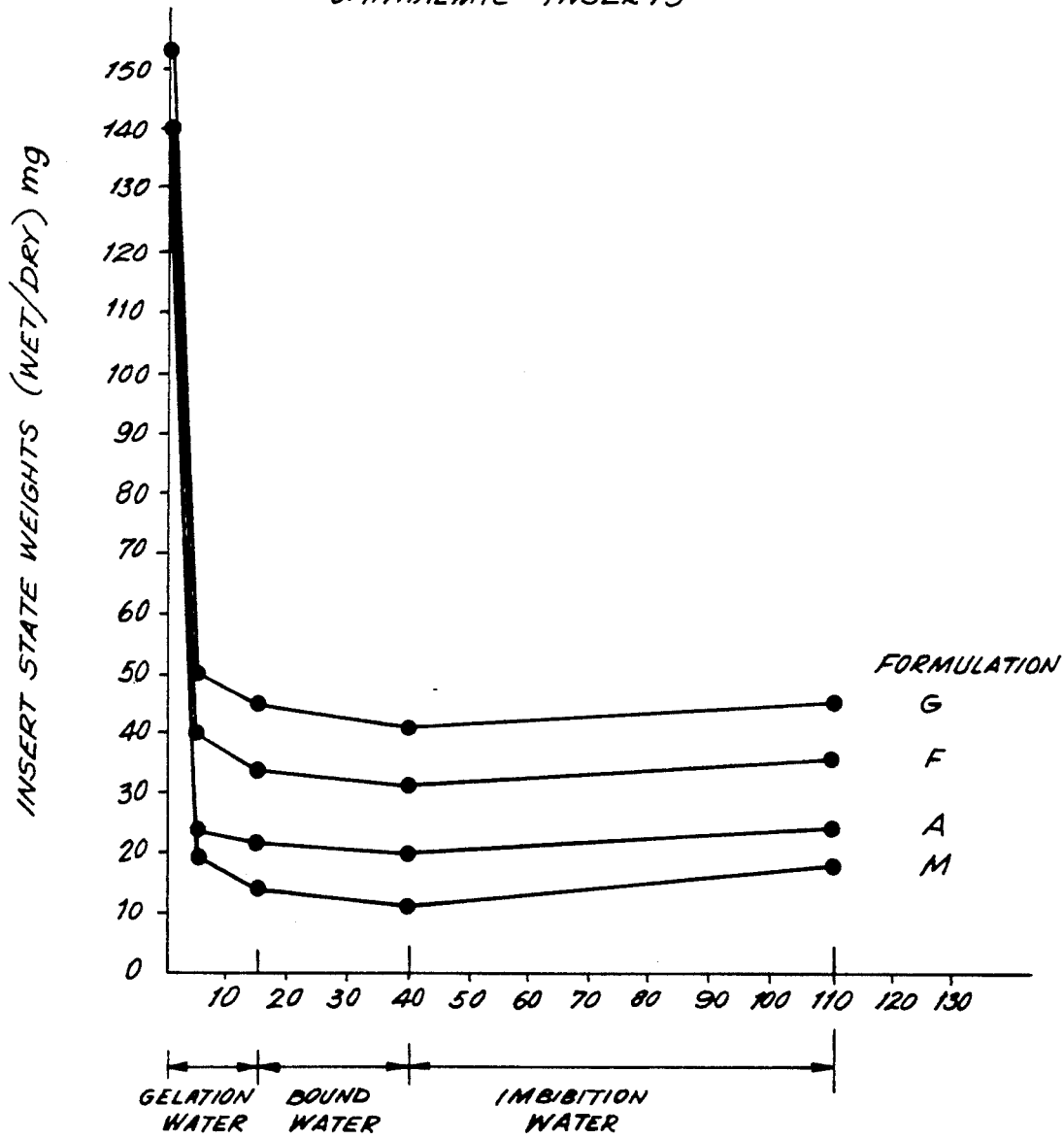
FIG. 1 is a graph showing comparative hydration data for various opthalmic inserts.

In order to obviate the conditions of bound excess water and high available surface area as well as diminish the rate of dissolution for increasing corneal contact time, a method for manufacturing a drug delivery rod insert is provided. The method includes the preparation of a paste-like hydrogel which, upon drying, results in the formation of xerogel inserts having mixed crystalline and amorphic concentration regions.

Specific drugs that may be used in accordance with the invention include, but are not limited to, methylcellulose, hydroxyethyl cellulose, alginic acid, a mixture of pilocarpine dispersed in methylcellulose and combinations of these polymers. In addition, the insert can include pilocarpine, timolol maleate, dexamethesone, antibiotics, sulpha drugs and, without limitation, any other drug that can be used in the eye in drop form.

In general, the chosen drug particles are formed into a paste by the addition of limited amounts of water in order to induce levigation, trituration and blending of the compounds to a pasty consistency. The ensuing mass is packed into and extruded through the hub orifice of a hypodermic syringe as continuous cylindrically shaped rod lengths, dried at room temperature and sectioned into small rod inserts. These cylindrical rod inserts are in contrast to the flat shaped flakes that are known in the prior art.

Table 1 shows various formulations for preparing a drug delivery rod insert in accordance with the invention (formulations A-L) and one prior art formulation (formulation M). The formulations include the amount of water soluble solid polymers and water used to form the paste. It is to be understood that these formulations are presented for purposes of illustration only and are not intended to be construed in a limiting sense.

TABLE 1

FORMULATIONS FOR PREPARING DRUG DELIVERY ROD INSERTS

| | | |
|---|---|---|
| A. Formulation (For Dry Eye Syndromes) | | |
| Methylcellulose powder (100 cps) | 5 | grams |
| Sterile Water For Injection, ad | 25 | ml |
| B. Formulation (For Dry Eye Syndromes) | | |
| Methylcellulose powder (400 cps) | 5 | grams |
| Sterile Water For Injection, ad | 25 | ml |
| C. Formulation (For Dry Eye Syndromes) | | |
| Methylcellulose powder (4000 cps) | 5 | grams |
| Sterile Water For Injection, ad | 25 | ml |
| D. Formulation (For Dry Eye Syndromes) | | |
| Hydroxyethyl cellulose | 5 | grams |
| Sterile Water For Injection, ad | 25 | ml |
| E. Formulation (For The Treatment of Glaucoma) | | |
| Pilocarpine Nitrate or Chlorine Salt powder | 2.5 | grams |
| Methylcellulose powder (4000 cps) | 5.0 | grams |
| Sterile Water For Injection, ad | 25.0 | ml |
| F. Formulation (For Dry Eye Syndromes) | | |
| Methylcellulose powder (4000 cps) | 5 | grams |
| Sterile Water For Injection, ad | 15 | ml |
| G. Formulation (For Dry Eye Syndromes) | | |
| Methylcellulose powder (4000 cps) | 5 | grams |
| Sterile Water For Injection, ad | 10 | ml |
| H. Formulation (For Dry Eye Syndromes) | | |
| Methylcellulose powder (4000 cps) | 2.5 | grams |
| Alginic Acid Powder | 2.5 | grams |
| Sterile Water For Injection, ad | 25.0 | ml |
| I. Formulation (For Dry Eye Syndromes) | | |
| Methylcellulose powder (4000 cps) | 2.5 | grams |
| Alginic Acid Powder | 2.5 | grams |
| Sterile Water For Injection, ad | 15.0 | ml |
| M. Formulation (For Dry Eye Syndromes) | | |
| Methylcellulose powder (4000 cps) | 1.0 | grams |
| Sterile Water For Injection, gs | 100.0 | ml |

Although formulation E discloses specific amounts of pilocarpine nitrate and salt, it is to be understood that varying amounts may be used. Additionally, although specific viscosity grades of methylcellulose and hydroxyethyl cellulose are provided in all the formulations, it is to be understood that varying viscosity grades may be used.

In formulations H and I, dispersion of the powdered drug in water, which functions as a plasticizer, is enhanced due to the addition of alginic acid powder. Accordingly, a rod insert which includes alginic acid powder as an active ingredient or as a plasticizer will have a more uniform distribution of drug material.

If methylcellulose, hydroxyethyl cellulose or alginic acid are the water soluble solid polymers, the compounds are triturated in a mortar and then blended with the water until the mass assumes a paste-like consistency or a viscous gel appearance.

If pilocarpine-methylcellulose is the water soluble solid polymer, pilocarpine is first dissolved in water to form a solution. The solution is added to methylcellulose powder or to a combination of polymers and is then triturated in a mortar until the mass assumes a paste-like consistency or a viscous gel appearance.

After the paste is prepared, it is packed and extruded as a wet gel from the barrel of a 10 ml or larger disposable plastic or glass syringe having a hub orifice equal to or greater than 2. mm. Alternatively, the paste may be packed in a cylindrical extrusion type apparatus rather than in a syringe.

After the paste is packed in the barrel, the plunger of the syringe is inserted and a sufficient amount of pressure is applied to extrude a continuous length of gel paste onto a flat hard surface. After the paste is partially dried, sections are cut using a cutting tool such as a scalpel, razor, microtome or the like, in order to form ophthalmic rod inserts. The length of the rod inserts ranges between about 0.1 mm and 2 mm.

After sectioning, the rod inserts are placed onto a clean dry glass or other suitable surface such as plastic or metal. One method of drying is to attach a vacuum hose to the end of a conical funnel stem so that the funnel is placed over the rod inserts in a manner that allows a space of approximately 0.5 mm to be maintained between the surface of the glass plate and the funnel cone. Vacuum is applied so that the rod inserts are suspended in a stream of insurgent air in the interior area of the cone. Alternate drying techniques may also be employed, such as drying at controlled room temperature (15°-30° C.) or under accelerated heating at 50°-75° C., and the method of the invention is not limited by the particular drying technique employed.

The dried rod inserts are sterilized using dry heat sterilization. The technique is employed at a temperature of between about 160° and 170° C. for a period of about two hours in order to assure complete sterilization of the insert.

After sterilization, the rods are individually packaged in gelatin capsules that have been air cleaned using filtered air. The capsule may be a number 0 to 4 type gelatin and may be clear, colored and/or opaque in appearance.

After packaging, the insert may be easily introduced into the cul-de-sac of the eye by either a physician or patient. The physician or patient separates the ends of the enclosed gelatin capsule while keeping the insert confined in the longer body segment of the capsule. He then withdraws the inferior cul-de-sac and drops the insert into the lower interior part of the eyelid. This method is superior to using forceps since the capsule body is maintained at a safe distance from the eye of the patient.

After the insert is placed within the cul-de-sac of the eye, the insert begins to swell at its outermost surface while maintaining a rod like shape in the core. Consequently, drug release via a diffusion process is slow and insert residency within the eye is prolonged. While in the eye, the insert is transported around the eyeball by tearing or blinking.

Clinical use of a drug delivery rod insert in accordance with the invention produces a sufficiently sustained therapeutic response. In tests, the insert continued to deliver medication long after it was inserted in the eye, up to a period of about 30 days. In contrast, an insert prepared by completely dissolving drug particles in water dissolved in the eye within a period of about 24 hours.

This finding may be explained by the difference in the water content between an insert manufactured by completely dissolving the drug particles in solution (total solution method) and applicants' invention (limited hydration process). The following experiment was carried out.

Inserts prepared via the total solution (Formulation M) method were formed using methylcellulose 4000 cps by dispersing 1% (w/v) of the powder in pre-heated 75° C. sterile water for injection, USP followed by mechanical agitation to enhance wettability for a period of one hour. The resultant liquid dispersion was "shock" cooled in an ice bath for forty-five minutes and refrigerated for a period of twenty-four hours at 3°-5° C. to obtain an optically clear colloidal liquid. Representative aliquots of the resultant formulation were subsequently transferred onto the surface of a glass Petri dish and subjected to evaporation at an accelerated temperature of 50° C. for a fifteen hour interval at which point a viscous nonhomogeneous type of fluid mass was observed. Heating was continued until the ensuing mass assumed a polymer: total insert normalized weight ratio of 16.6%, simulating for purposes of analogy the lowest proportion of active ingredient present in Formulation type A, for inserts prepared via the limited hydration (paste) technique of applicants' invention.

Following this treatment phase, 47 mm lengths of all gels (Formulations A,F,G and M) were respectively extruded from packed syringes onto the surfaces of Millipore glacine type filter pad backings and allowed to dehydrate at controlled room temperature (CRT; 25° C.) for fifteen hours followed by stressful heating at 50° C. for an additional twenty-five hours with dehydration being monitored as a function of time until each mass assumed constancy in weight. Following this period, the dry insert lengths were transferred to a CRT environment and allowed to equilibrate for periods of seventy-two hours prior to undertaking measurements on water vapor imbibition by the respective inserts.

Initial CRT dehydration (liquid: wet gel transition) established gelation water state. 50° C. drying ascertained degree of bound water and terminal CRT equilibration periods reflect moisture content of inserts exposed to normal ambient conditions of storage.

Data advanced in FIG. 1 and Table 2 below clearly establish significantly lower water levels present in inserts prepared via the limited hydration gel method in comparison to inserts prepared from solution.

TABLE 2

Water levels of Ophthalmic inserts dried under controlled room temperature (CRT) and at accelerated heating at 50° C. Summary of % Water Change

| Temperature °C. | Exposure Period (hr) | Hydration State of Inserts | Formulation | | | |
|---|---|---|---|---|---|---|
| | | | A | F | G | M* |
| CRT | 15 | Gelation Water | −84 | −74 | −66 | −92 |
| 50° C. | 25 | Bound Water | −9 | −6 | −4 | −19 |
| CRT | 70 | Imbibition Water | +20 | +12 | +7 | +40 |

*Normalized/wet gel basis at 16.6% polymer: insert ratio content following dehydration at CRT (controlled room temperature- 25° C.); negative (−) sign indicative of water loss; positive (+) symbol water uptake at each respective hydration state. Formulation (H) = 22% water content; Formulation (I) = 13% water content.

In Table 2, water content was determined by comparing the difference in weights via direct dehydration at 50° C. followed by a three day period in which the insert (M-I) was maintained in an environment of room temperature air. The results clearly establish that the limited hydration process produces opthalmic inserts containing significantly less water than inserts manufactured by the total solution method.

The preparation of the M gel mass, in accordance with the total solution methodology (TSM), results in the formation of a very "wet" and highly "swollen" gel structure during the pre-extrusion stages of production. This is in contrast to the firmly compacted and not as extensively or sparingly hydrated mass formed via the limited hydration technique (LHM). Inserts prepared by the LHM technique have a mass:volume relationship that is significantly greater than the mass:volume relationship of inserts prepared by the TSM technique. The net effect, under constant conditions of comparable extruded gel surface areas will be that TSM lengths of gel, upon drying at a fixed temperature and unit time, will yield inserts having significantly less weight than LHM cylindrical type rods. One, therefore, must not only be aware of absolute w/w relationships, but also of the very important spatial parameter of the prepared gel finished volume which influences the concentration gradient of both types of gel.

For a true comparison, a common denominator of equal surface area of extruded lengths must be introduced. Arriving at a 16.6% w/w normalized gel ratio prior to extrusion does not mean the respective inserts subsequently extruded and subjected to dehydration at two different thermal environments for purposes of estimating both gelation and bound water levels in the gel will be in a 1:5 ratio. Since the degree of swelling or positive volume change in the TSM insert is significantly greater than that found in the LHM gel, the two extruded inserts will not reach equal weights following the drying cycles and as expected the LHM dosage form will exhibit greater weight.

The percents of water levels can be ascertained using the relationship:

$$\% \Delta H_2O = ((w_f^{t2} - w_i^{t1})/w_i^{t1})10^2$$

$$(t_0 \rightarrow t_T)$$

where the percent change (% H$_2$O) from time $t_0$ to time $t_T$ is reflected by the difference in final and initial mass states (w$_{f,i}$) at each respective hydrated plateau state.

One cannot look only at absolute total % change values of water lost without reference to their states of mass. There is a significant difference between the two types of inserts when compared relative to their mass under anhydrous conditions as used in the dehydration process, i.e., at 12 and 20 mg respectively. These percents have to be viewed in terms of total dry mass.

Most importantly, one should focus on the final state of each insert, i.e., the imbibition periods. It is this region that largely determines the finished state of hydration of the inserts. As can be seen from the data, there is a two-fold difference between the two types of inserts in this region. The magnitude of this difference is controlled primarily by the pre-extrusion treatments to which the systems have been subjected in the preparatory stages of the respective gels which influences their basic matrix structures, thereby, setting the stage for rehydration to occur.

Rod inserts manufactured in accordance with the limited hydration method of the invention preferably have a surface area less than about 2.7 mm² in order to allow for maximum comfort and adequate contact time. In contrast, conventional eye inserts have a surface area ranging between about 5 and 80 mm². As the rod insert described herein has considerably less surface area for contact with lacrimal fluids, dissolution of the insert after placement in the eye can be expected to be inhibited.

For the treatment of dry eye syndrome, it is preferred that the water soluble solid polymer be methylcellulose since methylcellulose is more hydrophobic, thereby leading to diminished solubility. In order to demonstrate this property, experiments were conducted to compare the dissolution and release characteristics, the rates of water loss, and the degree of water retention.

In order to compare the prolonged release and delayed drug delivery of a methylcellulose rod insert to a hydroxylated cellulose insert, static dissolution experiments using Technicon Analyzer 2 m cup stations were carried out in 0.9% isotonic sodium chloride. The experiments were conducted at room temperature for similar time periods.

The results of the experiment indicate that a methylcellulose insert exhibits significantly less dissolution in comparison with a hydroxyethyl cellulose insert. Additionally, the methylcellulose insert maintains its rod like shape for a significantly greater time interval. Upon examination, the macroscopic appearance of the methylcellulose insert was that of a rod shaped structure, in contrast to the hydroxyethyl cellulose insert which exhibited physical shape disruption within 30 minutes of exposure. Furthermore, after further examination, the methylcellulose insert has a solid rod core in the interior of the gel matrix whereas the hydroxylated insert shows evidence of complete gelation.

In order to further show the advantage in using a methylcellulose rod insert, additional studies were conducted using sections of wet extruded inserts. The result showed the presence of a solid core in the interior of the rod even after a time period of about 90 minutes. Thus, the methylcellulose rod insert maintains its physical integrity for a prolonged duration, suggesting prolonged in vivo release time.

In order to compare the rate of water loss in a methylcellulose rod insert to a hydroxylated rod, 84 square mm wet cylindrical rod of methylcellulose 100 cps, 400 cps, 4000 cps, hydroxyethyl cellulose and mixtures of methylcellulose with pilocarpine were examined in order to determine their rates of dehydration. Individual rods were placed on a Millipore GS 0.22 micron filter pad backing and total weight loss was determined as a function of time at a room temperature of about 24° C.

Figure 2:
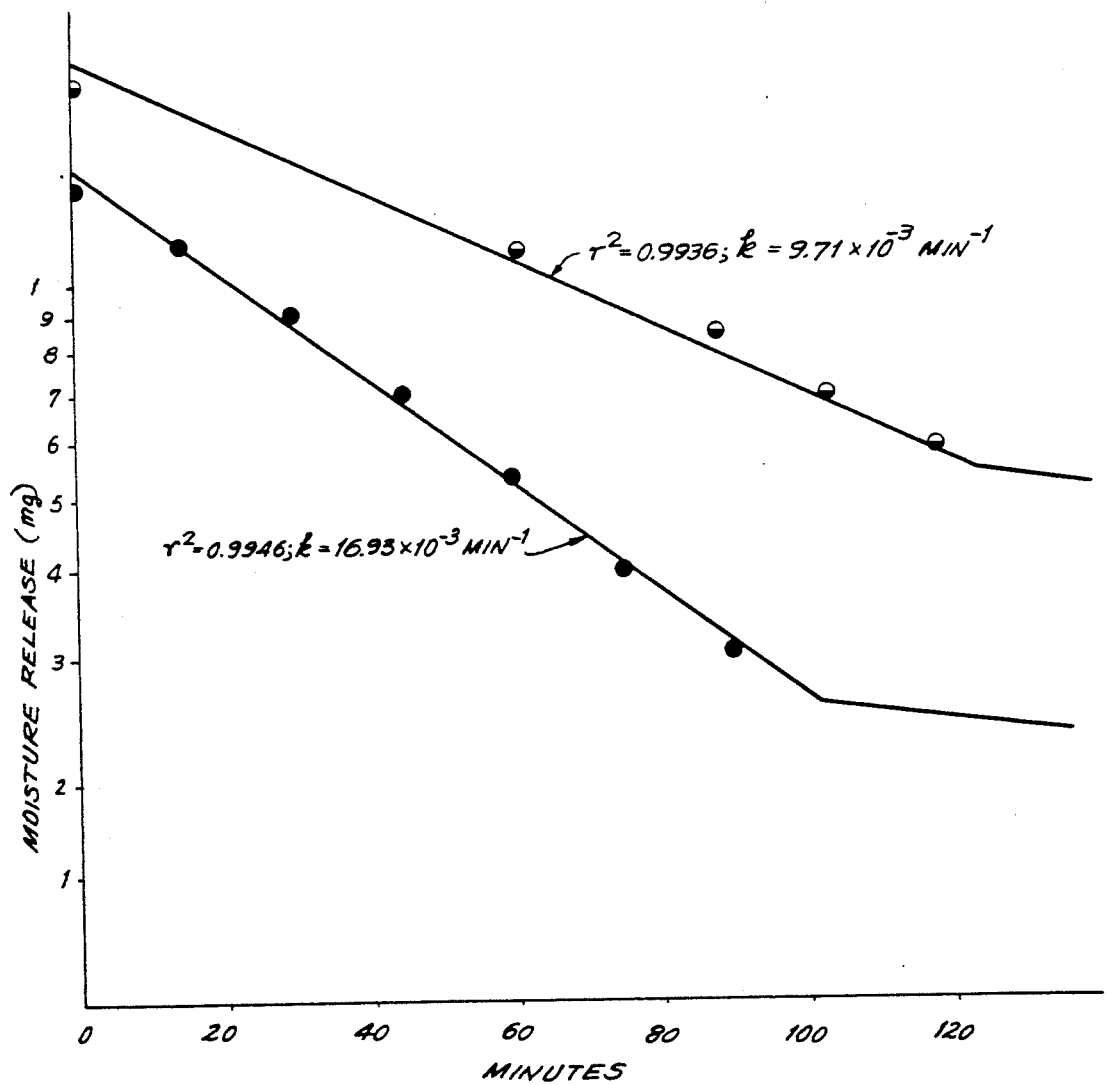
FIG. 2 is a graph showing the rates of water vapor loss of methylcellulose rod inserts and hydroxyethyl cellulose rod inserts.

Reference is now made to FIG. 2 which illustrates the results of the dehydration experiments. For each ingredient, the rods were examined over the transition wet-dry interval for a period of approximately 2 hours. For the methylcellulose rods, the transition point was determined to be about 75 minutes; for the hydroxylated rods, the transition point was determined to be about 135 minutes. Additionally, the hydroxylated rods lost significantly greater amounts of water over a given time period when compared to the methylcellulose rods.

FIG. 2 shows that the drying rates of the methylcellulose rods obtained from first order plotting of moisture loss against time produce rate constants $K_1$ and $K_2$ to be equal to about $9.71 \times 10^{-3}$ min$^{-1}$ for the hydroxylated rods and $16.93 \times 10^{-3}$ min$^{-1}$ for the methylcellulose rods, respectively, or approximately twice as great for methylcellulose rods. Additionally, rods made of methylcellulose 400 cps, methylcellulose 100 cps, methylcellulose 4000 cps and pilocarpine-methylcellulose 4000 cps exhibited no significant difference in the rate of dehydration.

In order to compare the degree of water retention in methylcellulose rods to hydroxyethyl cellulose rods, water entrapment tests at controlled room temperature were carried out on a 94 mm² rod inserts. The rods contained the water soluble solid polymers recited in Table 3 below.

TABLE 3

| Dosage Form | Wet Wgt (mg) | Gum Content (mg) | Dry Wet (mg) | $H_2O$ (mg) | Normalized* (mg) | $H_2O$ (%) |
|---|---|---|---|---|---|---|
| Methylcellulose 100 | 117 | 19.50 | 23 | +3.50 | +3.76 | +17.9 |
| Methylcellulose 400 | 127 | 21.20 | 25 | +3.80 | +3.76 | +17.0 |
| Methylcellulose 4000 | 137 | 22.83 | 25.1 | +2.27 | +2.09 | +9.9 |
| Methylcellulose 4000 Pilocarpine | 131 | 20.15 / 10.08 / 30.23 | 34.3 | +4.07 | +2.83 | +13.5 |
| Hydroxyethylcellulose | 190 | 31.66 | 46 | +14.34 | +9.51 | +45.3 |

*Normalized to a 21 mg dry weight basis; Pilocarpine as the nitrate salt; % $H_2O$ (uptake) = [$H_2O$ (mg)/gum content] × 100; Surface area = SA (mm²) = $2 \pi r^2 + 2 \pi rL$, where r and L represent the radius and length, respectively, of a solid cylindrical mass.

Table 3 shows that hydroxyethylcellulose rod inserts have a water uptake value of at least two and one-half times greater than the value for the lower viscosity methylcellulose rods and about five times greater than the highest viscosity grade results.

Since dissolution is significantly greater for rods containing hydroxylated compounds than rods containing methylcellulose compounds, methylcellulose and methylcellulose pilocarpine inserts manufactured in accordance with the invention have improved physical and chemical properties and are therefore the preferred water soluble solid polymer of a rod insert manufactured in accordance with the invention.

It will thus be seen that the objects set forth above, among those made apparent from the preceding description, are efficiently obtained and, since certain changes may be made in carrying out the above method and in the composition set forth without departing from the spirit and scope of the invention, it is intended that all matter contained in the above description and shown in the accompanying drawings shall be interpreted as illustrative and not in a limiting sense.

It is also to be understood that the following claims are intended to cover all the generic and specific features of the invention herein described and all statements of the the scope of the invention which, as a matter of language, might be said to fall therebetween.

Particularly it is to be understood that in said claims, ingredients or compounds recited in the singular are intended to include compatible mixtures of such ingredients or compounds wherever the sense permits.

What is claimed is:

1. A method for preparing an ophthalmic insert capable of releasing a desired amount of therapeutic substance into the eye of a patient comprising the steps of:
adding an amount of water to a therapeutically effective amount of a water soluble solid polymer of a therapeutic substance suitable for use in said insert sufficient to form a paste;
extruding said paste;
sectioning said extruded paste; and
drying said sectioned extruded paste to form a plurality of said inserts.

2. The method according to claim 1, wherein said inserts are rod shaped.

3. The method according to claim 2, wherein each of said inserts has a length between about 0.1 to 2.0 mm.

4. The method according to claim 3, wherein said length is between about 0.1 to 0.2 mm.

5. The method according to claim 2, wherein each of said inserts has a surface area less than about 2.7 mm².

6. The method according to claim 3, wherein said water soluble solid polymer is selected from the group consisting of methylcellulose, hydroxyethyl cellulose, alginic acid and mixtures thereof.

7. The method according to claim 6, wherein said water soluble solid polymer is methylcellulose.

8. The method according to claim 7, wherein said methylcellulose has a viscosity grade between about 100 to 400 cps.

9. The method according to claim 7, which further comprises adding alginic acid to said methylcellulose polymer during paste formation.

10. The method according to claim 7, which further comprises adding at least one compound selected from the group consisting of pilocarpine nitrate and hydrochloride salt to said methylcellulose during paste formation.

11. The method according to claim 6, wherein the proportion of water soluble solid polymer to water is about 1 gram of polymer to between about 2 and 5 milliliters of water.

12. The method according to claim 11, wherein said proportion is about 1 gram of polymer to 5 milliliters of water.

13. The method according to claim 1, further comprising drying said extruded paste prior to sectioning.

14. The method according to claim 11, wherein each of said inserts has a surface area less than about 3 mm².

15. The method according to claim 1 which further comprises adding a therapeutically effective amount of a medicant to the water soluble solid polymer during paste formation.

16. The method according to claim 15 wherein the medicant is selected from the group consisting of pilocarpine, timolol maleate, dexamethasone, antibiotics, and sulpha drugs.

17. The method according to claim 16 wherein the medicant is in particulate form.

* * * * *